United States Patent
Li et al.

(10) Patent No.: US 10,335,417 B2
(45) Date of Patent: Jul. 2, 2019

(54) THIAZIDEAMIDE DERIVATIVE AND USE THEREOF

(71) Applicant: Institute of Pharmacology and Toxicology Academy of Military Medical Sciences P.L.A. China, Beijing (CN)

(72) Inventors: Song Li, Beijing (CN); Junhai Xiao, Beijing (CN); Boqun Lyu, Beijing (CN); Hongqiang Wang, Beijing (CN); Wu Zhong, Beijing (CN); Lili Wang, Beijing (CN); Zhibing Zheng, Beijing (CN); Yunde Xie, Beijing (CN); Xinbo Zhou, Beijing (CN); Xingzhou Li, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/739,872

(22) PCT Filed: Jun. 28, 2016

(86) PCT No.: PCT/CN2016/087433
§ 371 (c)(1),
(2) Date: Dec. 26, 2017

(87) PCT Pub. No.: WO2017/000869
PCT Pub. Date: Jan. 5, 2017

(65) Prior Publication Data
US 2018/0185376 A1 Jul. 5, 2018

(30) Foreign Application Priority Data
Jun. 30, 2015 (CN) .......................... 2015 1 0373078

(51) Int. Cl.
C07D 279/12 (2006.01)
A61K 31/54 (2006.01)
A61P 25/28 (2006.01)
A61P 25/16 (2006.01)

(52) U.S. Cl.
CPC .............. *A61K 31/54* (2013.01); *A61P 25/16* (2018.01); *A61P 25/28* (2018.01); *C07D 279/12* (2013.01)

(58) Field of Classification Search
CPC .............................. A61K 31/54; C07D 279/12

USPC ...................................................... 514/227.5
See application file for complete search history.

(56) References Cited

U.S. PATENT DOCUMENTS

| | | | |
|---|---|---|---|
| 6,291,453 | B1 | 9/2001 | Ashwell et al. |
| 6,939,855 | B2 * | 9/2005 | Yednock .............. A61K 31/381 |
| | | | 514/1.1 |
| 7,304,057 | B2 * | 12/2007 | Li ......................... C07D 211/96 |
| | | | 514/227.5 |
| 9,359,312 | B2 | 6/2016 | Li et al. |
| 2005/0130958 | A1 | 6/2005 | Li et al. |
| 2015/0203460 | A1 | 7/2015 | Li et al. |

FOREIGN PATENT DOCUMENTS

| | | |
|---|---|---|
| CA | 2882289 A1 | 2/2014 |
| CN | 1422852 A | 6/2003 |
| WO | WO 2004/066931 A2 | 8/2004 |
| WO | WO 2014/029102 A1 | 2/2014 |

OTHER PUBLICATIONS

International Search Report (ISR) for PCT/CN2016/087433; I.A. fd: Jun. 28, 2016; dated Oct. 10, 2016, State Intellectual Property Office of the P.R. China, Beijing, China.
International Preliminary Report on Patentability (IPRP) (Chapter I of the Patent Cooperation Treaty) (PCT Rule 44*bis*) for PCT/CN2016/087433; I.A. fd: Jun. 28, 2016; dated Jan. 2, 2018, by The International Bureau of WIPO, Geneva, Switzerland.
Extended European search report including the Supplementary European search report and the European search opinion, dated Dec. 10, 2018, European Patent Office, Munich, Germany.

* cited by examiner

*Primary Examiner* — Kahsay Habte
(74) *Attorney, Agent, or Firm* — Sterne, Kessler, Goldstein & Fox P.L.L.C.

(57) ABSTRACT

The invention belongs to the technical field of medicines. In particular, the invention relates to a thiazideamide derivative compound or a pharmaceutically acceptable salt or solvate thereof, a pharmaceutical composition comprising the compound or a pharmaceutically acceptable salt or solvate thereof, a method for preparing the compound or a pharmaceutically acceptable salt or solvate thereof, and a use of the compound or a pharmaceutically acceptable salt or solvate thereof. For example, the compound or a pharmaceutically acceptable salt or solvate thereof according to the invention can be used to prevent and/or treat a neurodegenerative disease or a neuropathic disease caused by a physical trauma or a related disease.

5 Claims, No Drawings

THIAZIDEAMIDE DERIVATIVE AND USE THEREOF

TECHNICAL FIELD

The invention belongs to the technical field of medicines. In particular, the invention relates to a thiazideamide derivative compound or a pharmaceutically acceptable salt or solvate thereof, a pharmaceutical composition comprising the compound or a pharmaceutically acceptable salt or solvate thereof, a method for preparing the compound or a pharmaceutically acceptable salt or solvate thereof, and a use of the compound or a pharmaceutically acceptable salt or solvate thereof. For example, the compound or a pharmaceutically acceptable salt or solvate thereof according to the invention can be used to prevent and/or treat a neurodegenerative disease, or a neuropathic disease caused by a physical trauma or a related disease.

BACKGROUND ART

Neurodegenerative disease refers to a class of diseases caused by progressive pathological changes of nervous system, including Alzheimer's disease, Parkinson's disease, Huntington's disease, amyotrophic lateral sclerosis (ALS), etc. Since the cause for the development of this class of diseases is complex, and the pathogenic mechanism is not clear yet, there is no effective therapeutic agent yet.

FK506 binding proteins (FKBPs), named for the capability of binding to immunosuppressant FK506 (tacrolimus), are important mediators for FK506 to exert immunosuppressive action, and their physiological function has not been completely identified yet. Steiner J. P. et al. found in 1992 that the concentration of FKBPs in brain and periphery was much greater than that in immunologic tissues, and it was thus conjectured that there might be a certain relationship between FKBPs and nervous system. The results obtained by Dawson et al. show that FK506 can block nerve excitotoxicity caused by activation of NMDA receptor (N-methyl-D-aspartic acid receptor) by glutamic acid. It is supposed that this might be because after the inhibition of Calcineurin by FKBPs, the phosphorylation level of nitric oxide synthetase (NOS) increases, which inhibits the catalytic activity of NOS, thereby avoiding the injury of neurons by NO. In addition, it is found by studies that a protein closely associated with the growth of neurons—GAP43 (growth associated protein-43) is also a substrate for Calcinerin, the nerve regeneration of injured facial nerve and sciatic nerve is always accompanied by a significant increase in the mRNA level of GAP43, and meanwhile the mRNA level of FKBPs also increases correspondingly. These findings show that FKBPs may be associated with nerve growth. People are inspired by the above results and finally find organic small-molecule compounds capable of promoting nerve growth, from FKBPs ligands, and therefore FKBPs are also known as neuroimmunophilins.

Based on such an inventive concept, in 1994, Lyons et al. found by studies that immunosuppressive agent FK506 had a significant activity of promoting nerve growth in vitro, and set a precedent for research on small-molecule nerve growth promoters. Although the mechanism underlying the nerve growth promotion and protection of FKBP family ligands has not been identified completely yet, more and more studies show that FKBPs are involved in the mediation of the process. By evaluation using in vitro assays (such as chick embryonic dorsal root ganglion growth assay, PC 12 cell differentiation assay and assay on oxidative damage of nerve cell lines) and multiple animal models (such as rat peripheral sciatic nerve transected model, diabetes mellitus mouse model of peripheral neurodegenerative disease, animal model of Parkinson's disease and presenile dementia animal model), the results show that some compounds, which were designed based on FKBPs structures and synthesized, had significantly nerve growth-promoting and protective function. The typical one among these compounds is GPI1485 from Guilford Pharmaceuticals Inc. The Company uses GPI1485 as a prophylactic and therapeutic drug for Parkinson's disease and apoplexy, its phase II clinical research has finished, and the phase III clinical research is ongoing. Meanwhile, a lot of highly active compounds emerges constantly, and therefore FKBPs have become an important target for drugs for preventing and treating neurodegenerative diseases.

The Chinese Invention Patent ZL01142744.2 (Substituted 6-membered N-heterocyclic compounds and their uses as neurological regulator) discloses a class of FKBP ligands with new structures capable of promoting nerve regeneration, among which Compound 4 is the optimal compound. However, it is found by studies that Compound 4 has low blood-brain barrier penetration, low melting point, and is in a state of oil at room temperature and therefore is not suitable for use in the manufacture of a medicament for preventing/treating a neurodegenerative disease. The Chinese Invention Patent CN102675244 discloses its optimized compounds, however, they can be further improved with respect to the activity of promoting the growth of nerve fibers and in vivo efficacy.

Contents of Invention

In the description and claims of the present application, a compound is named based on its chemical structural formula. If the name of a compound used herein is not consistent with the chemical structural formula, the chemical structural formula will prevail.

In the invention, unless otherwise specified, the scientific and technical terms used herein have the meanings as generally understood by a person skilled in the art. Moreover, the laboratory operations used herein are the routine operations widely used in the corresponding fields. In addition, in order to better understand the invention, the definitions and explanations of the relevant terms are provided as follows.

As used herein, the term "thiazine" refers to a 6-membered ring structure containing four cyclic carbon atoms, one cyclic nitrogen atom and one cyclic sulfur atom, including, but not limited to 1,3-thiazine, 1,4-thiazine, dihydro-1,3-thiazine, dihydro-1,4-thiazine, tetrahydro-1,3-thiazine, tetrahydro-1,4-thiazine, etc. The term "thiazideamide" refers to a thiazine structure substituted by amide group.

The term "$C_{1-4}$alkyl" as used in the invention refers to a linear or branched alkyl containing 1-4 carbon atoms, including, but not limited to $C_{1-2}$alkyl, $C_{1-3}$alkyl, $C_{2-4}$alkyl, e.g., methyl, ethyl, n-propyl, isopropyl, n-butyl, sec-butyl, tert-butyl, isobutyl, etc.

The term "$C_{1-4}$alkoxy" as used in the invention refers to a group wherein $C_{1-4}$alkyl is linked to another structure via an oxygen atom, including, but not limited to $C_{1-2}$alkoxyl, $C_{1-3}$alkoxyl, $C_{2-4}$ alkoxyl, e.g., methoxy, ethoxy, n-propoxy, isopropoxy, n-butoxy, sec-butoxy, tert-butoxy, isobutoxy, etc.

The term "pharmaceutically acceptable salt" as used in the invention includes, but not limited to inorganic salt such as hydrochlorate, hydrobromate, hydriodate, nitrate, sulfate, bisulfate, phosphate, and biphosphate; and organic salt, such as acetate, propionate, butyrate, oxalate, trimethyl acetate, oxalate, alginate, citrate, picrate, gluconate, tartrate, maleate, methanesulfonate, succinate, and pamoate.

A "solvate" of the compound according to the invention refers to a substance formed by the association of the compound with solvent molecule(s). The solvent may be an organic solvent (e.g., methanol, ethanol, propanol, acetonitrile, etc.), water, etc. For example, the compound of Formula (I) according to the invention may form an alcoholate with ethanol, or form a hydrate with water.

The term "neurodegenerative diseases" as used in the invention refers to a disease caused by progressive pathologic changes of nervous system, including, but not limited to Alzheimer's disease, Parkinson's disease, Huntington's disease, amyotrophic lateral sclerosis and marrowbrain multiple sclerosis.

The term "physical trauma" as used in the invention includes, but not limited to heat injury, cold injury, mechanical injury and electric injury.

The term "neuropathy caused by a related disease" as used in the invention includes, but not limited to neuropathy caused by acquired immunodeficiency, neuropathy caused by diabetes mellitus and neuropathy caused by stroke.

The term "an effective amount" as used in the invention refers to an amount that is sufficient to achieve or at least partially achieve a desired effect. For example, an effective amount for preventing a disease (e.g., a neurodegenerative disease, a neuropathy caused by a physical trauma, or a neuropathy caused by a related disease) refers to an amount that is sufficient to prevent, suppress or delay the development of the disease (e.g., a neurodegenerative disease, a neuropathy caused by a physical trauma, or a neuropathy caused by a related disease); a therapeutically effective amount refers to an amount that is sufficient to cure or at least partially suppress a disease and its complications in a patient with the disease. The determination of such an effective amount is completely within the ability of a person skilled in the art. For example, an amount effective for a therapeutic use depends on the severity degree of a disease to be treated, general state of the immune system in a patient, general conditions of a patient, such as age, weight and gender, administration means of drugs, additional therapies used simultaneously, and the like.

The term "about" as used in the invention shall be understood by a person skilled in the art, and shall vary to a certain extent based on the context. If the term is not clear for a person skilled in the art based the context, the term "about" means having a deviation no more than ±10% of the specific numerical value or range.

By conducting deep studies and paying creative work, the inventor obtained a thiazideamide derivative. The inventor found that by suitable selection of R1, R2 and/or R3 groups in the thiazideamide derivative of Formula (I), the resultant compound has several aspects improved relative to the existing thiazideamide derivative, such as neurotrophic activity, in vivo efficacy and/or the ability of passing through blood-brain barrier in mice with apoplexy. Therefore, the following invention is provided:

In an aspect, the invention provides a compound of Formula (I), or a pharmaceutically acceptable salt or solvate thereof,

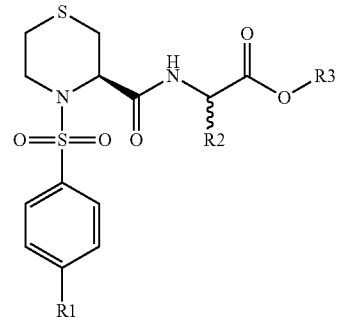

wherein,
R1 is selected from $C_{1-4}$alkyl;
R2 and R3 are independently selected from $C_{1-4}$alkyl, optionally, the $C_{1-4}$alkyl is substituted with a phenyl;
optionally, the phenyl is substituted with a substituent selected from the group consisting of $C_{1-4}$alkyl, $C_{1-4}$alkoxyl, hydroxyl, amino and carboxyl.

In a preferred embodiment, R2 has an "R" configuration.
In a preferred embodiment, R2 has an "S" configuration.
In a preferred embodiment, R1 is selected from $C_{2-3}$alkyl, e.g., ethyl, n-propyl, isopropyl.
In a more preferred embodiment, R1 is ethyl.
In a preferred embodiment, R2 and R3 are independently selected from $C_{1-4}$alkyl, e.g., methyl, ethyl, n-propyl, isopropyl, n-butyl, sec-butyl, tert-butyl, isobutyl.
In a preferred embodiment, R2 is selected from $C_{3-4}$alkyl, e.g., n-propyl, isopropyl, n-butyl, sec-butyl, tert-butyl, isobutyl.
In a preferred embodiment, R2 is isobutyl.
In a preferred embodiment, R3 is selected from $C_{1-3}$alkyl, e.g., n-propyl, isopropyl, n-butyl, sec-butyl, tert-butyl, isobutyl.
In a preferred embodiment, R3 is selected from $C_{1-3}$alkyl, e.g., methyl, ethyl, n-propyl, isopropyl.
In a preferred embodiment, R3 is isopropyl.
In a preferred embodiment, R2 has an "R" configuration.
In a preferred embodiment, R2 has an "S" configuration.
In a preferred embodiment, R2 is selected from $C_{1-4}$alkyl (e.g., $C_{1-2}$alkyl), and the $C_{1-4}$alkyl (e.g., $C_{1-2}$alkyl) is substituted with phenyl, optionally, the phenyl is substituted with a substituent selected from the group consisting of $C_{1-4}$alkyl, $C_{1-4}$alkoxyl, hydroxyl, amino and carboxyl.
In a preferred embodiment, R2 is benzyl.
In a preferred embodiment, R2 is phenethyl.
In a preferred embodiment, R1 is methyl.
In a preferred embodiment, R3 is methyl, ethyl, isopropyl, tert-butyl or benzyl.
In a preferred embodiment, R3 is methyl, ethyl, isopropyl or tert-butyl.
In a preferred embodiment, R3 is methyl.
In a preferred embodiment, R3 is ethyl.
In a preferred embodiment, R3 is isopropyl.
In a preferred embodiment, R3 is tert-butyl.
In a preferred embodiment, R3 is benzyl.
In a more preferred embodiment, R1 is methyl; R2 is benzyl or phenethyl; R3 is methyl, ethyl, isopropyl, tert-butyl or benzyl.
In a more preferred embodiment, R1 is methyl; R2 is benzyl or phenethyl; R3 is methyl, ethyl, isopropyl or tert-butyl.
In a preferred embodiment, R2 has an "R" configuration.

In a preferred embodiment, R2 has an "S" configuration.
In a preferred embodiment, R1 is methyl.
In a preferred embodiment, R2 is benzyl.
In a preferred embodiment, R2 is phenethyl.
In a preferred embodiment, R3 is ethyl.
In a preferred embodiment, R3 is isopropyl.
In a preferred embodiment, R3 is tert-butyl.
In a more preferred embodiment, R1 is methyl; R2 is benzyl or phenethyl; R3 is ethyl, isopropyl or tert-butyl.
In a preferred embodiment, R1 is methyl; R2 is benzyl or phenethyl; R3 is ethyl.
In a preferred embodiment, R1 is methyl; R2 is benzyl or phenethyl; R3 is isopropyl.
In a preferred embodiment, R1 is methyl; R2 is benzyl or phenethyl; R3 is tert-butyl.
In a preferred embodiment, R1 is methyl; R2 is benzyl; R3 is ethyl, isopropyl, or tert-butyl.
In a preferred embodiment, R1 is methyl; R2 is phenethyl; R3 is ethyl, isopropyl or tert-butyl.
In a preferred embodiment, R2 has an "R" configuration.
In a preferred embodiment, R2 has an "S" configuration.
In a preferred embodiment, R1 is methyl.
In a preferred embodiment, R2 is selected from $C_{2-4}$alkyl, e.g., ethyl, n-propyl, isopropyl, n-butyl, sec-butyl, tert-butyl, isobutyl.
In a preferred embodiment, R2 is selected from $C_{3-4}$alkyl, e.g., n-propyl, isopropyl, n-butyl, sec-butyl, tert-butyl, isobutyl.
In a preferred embodiment, R2 is isopropyl.
In a preferred embodiment, R2 is sec-butyl.
In a preferred embodiment, R3 is methyl, ethyl, tert-butyl or benzyl.
In a preferred embodiment, R3 is methyl, ethyl or tert-butyl.
In a preferred embodiment, R3 is methyl.
In a preferred embodiment, R3 is ethyl.
In a preferred embodiment, R3 is tert-butyl.
In a preferred embodiment, R3 is benzyl.
In a more preferred embodiment, R1 is methyl, R2 is selected from $C_{2-4}$alkyl; R3 is methyl, ethyl, tert-butyl or benzyl.
In a more preferred embodiment, R1 is methyl, R2 is selected from $C_{3-4}$alkyl; R3 is methyl, ethyl, tert-butyl or benzyl.
In a more preferred embodiment, R1 is methyl, R2 is isopropyl or sec-butyl; R3 is methyl, ethyl, tert-butyl or benzyl.
In a preferred embodiment, R2 has an "R" configuration.
In a preferred embodiment, R2 has an "S" configuration.
In a preferred embodiment, R1 is methyl, R2 is isopropyl, R3 is methyl, ethyl or tert-butyl.
In a preferred embodiment, R1 is methyl, R2 is sec-butyl, R3 is methyl, ethyl or tert-butyl.
In a preferred embodiment, R1 is methyl, R2 is isopropyl or sec-butyl, R3 is methyl.
In a preferred embodiment, R1 is methyl, R2 is isopropyl or sec-butyl, R3 is ethyl.
In a preferred embodiment, R1 is methyl, R2 is isopropyl or sec-butyl, R3 is tert-butyl.
In a preferred embodiment, R2 has an "R" configuration.
In a preferred embodiment, R2 has an "S" configuration.
Some compounds of the invention are shown in the following table.

Some Compounds of the Invention

| Compound No. | Structure | Name |
|---|---|---|
| 7 | 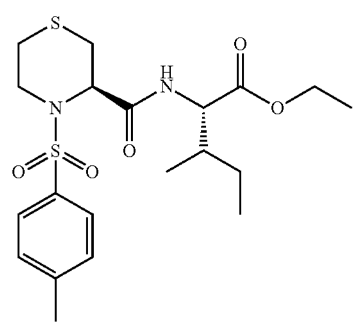 [SMILES: CCOC(=O)[C@@H](NC(=O)[C@@H]1CSCCN1S(=O)(=O)c1ccc(C)cc1)C(C)CC] | (2S,3R)-ethyl-3-methyl-2((R)-(4-methylphenyl)sulfonyltetrahydro-1,4-thiazin-3-aminoformyl)valerate |
| 8 | 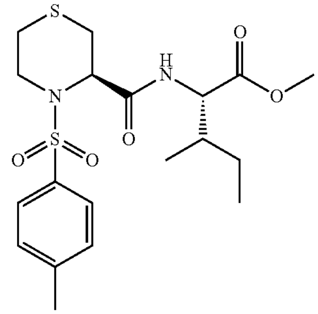 [SMILES: CCC(C)[C@H](NC(=O)[C@@H]1CSCCN1S(=O)(=O)c1ccc(C)cc1)C(=O)OC] | (2S,3R)-methyl-3-methyl-2((R)-(4-methylphenyl)sulfonyltetrahydro-1,4-thiazin-3-aminoformyl)valerate |

-continued

| Compound No. | Structure | Name |
|---|---|---|
| 9 | 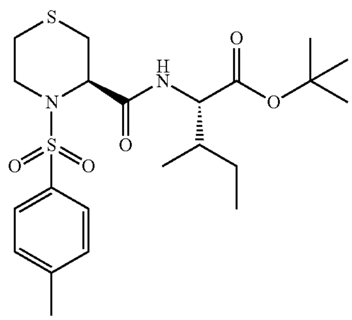 [SMILES: CCC(C)[C@H](NC(=O)[C@@H]1CSCCN1S(=O)(=O)c1ccc(C)cc1)C(=O)OC(C)(C)C] | (2S,3R)-tert-butyl-3-methyl-2((R)-(4-methylphenyl)sulfonyltetrahydro-1,4-thiazin-3-aminoformyl)valerate |
| 10 | 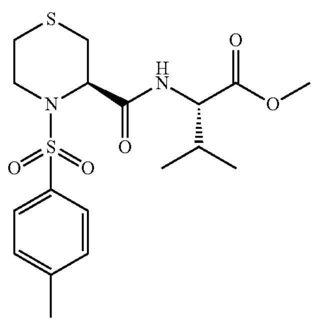 [SMILES: COC(=O)[C@@H](NC(=O)[C@@H]1CSCCN1S(=O)(=O)c1ccc(C)cc1)C(C)C] | (S)-methyl-3-methyl-2((R)-(4-methylphenyl)sulfonyltetrahydro-1,4-thiazin-3-aminoformyl)butyrate |
| 11 | 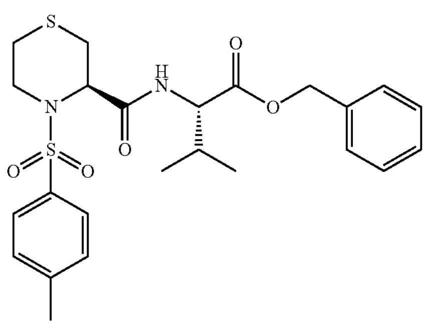 [SMILES: Cc1ccc(S(=O)(=O)N2CCSC[C@H]2C(=O)N[C@H](C(=O)OCc2ccccc2)C(C)C)cc1] | (S)-benzyl-3-methyl-2((R)-(4-methylphenyl)sulfonyltetrahydro-1,4-thiazin-3-aminoformyl)butyrate |
| 12 | 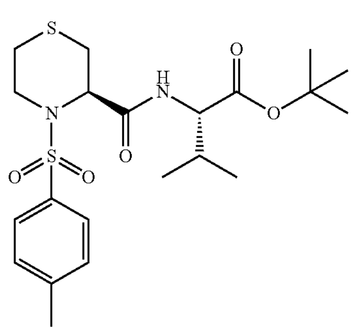 [SMILES: Cc1ccc(S(=O)(=O)N2CCSC[C@H]2C(=O)N[C@H](C(=O)OC(C)(C)C)C(C)C)cc1] | (S)-tert-butyl-3-methyl-2((R)-(4-methylphenyl)sulfonyltetrahydro-1,4-thiazin-3-aminoformyl)butyrate |

| Compound No. | Structure | Name |
| --- | --- | --- |
| 13 | 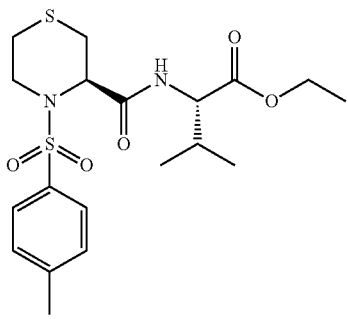 [SMILES: CCOC(=O)[C@@H](NC(=O)[C@@H]1CSCCN1S(=O)(=O)c1ccc(C)cc1)C(C)C] | (S)-ethyl-3-methyl-2((R)-(4-methyl-phenyl)sulfonyltetrahydro-1,4-thiazin-3-aminoformyl)butyrate |
| 14 | 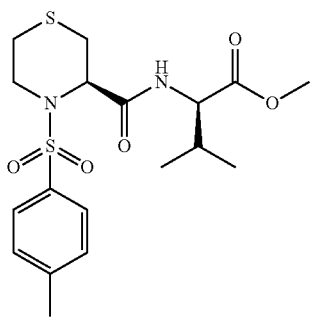 [SMILES: COC(=O)[C@H](NC(=O)[C@@H]1CSCCN1S(=O)(=O)c1ccc(C)cc1)C(C)C] | (R)-methyl-3-methyl-2((R)-(4-methyl-phenyl)sulfonyltetrahydro-1,4-thiazin-3-aminoformyl)butyrate |
| 15 | 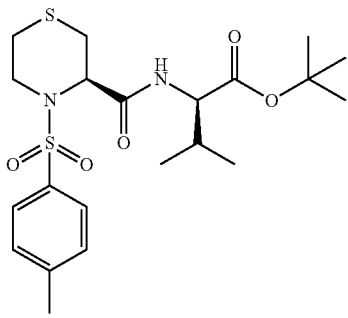 [SMILES: Cc1ccc(S(=O)(=O)N2CCSC[C@H]2C(=O)N[C@@H](C(=O)OC(C)(C)C)C(C)C)cc1] | (R)-tert-butyl-3-methyl-2((R)-(4-methylphenyl)sulfonyltetrahydro-1,4-thiazin-3-aminoformyl)butyrate |
| 16 | 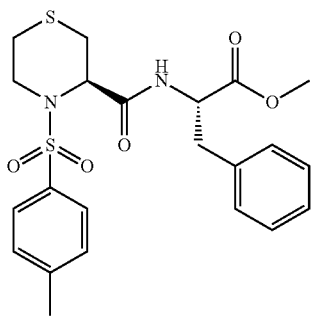 [SMILES: COC(=O)[C@H](Cc1ccccc1)NC(=O)[C@@H]1CSCCN1S(=O)(=O)c1ccc(C)cc1] | (S)-methyl-3-phenyl-2((R)-(4-methyl-phenyl)sulfonyltetrahydro-1,4-thiazin-3-aminoformyl)propionate |

|  Compound No. | Structure | Name |
| --- | --- | --- |
| 17 | 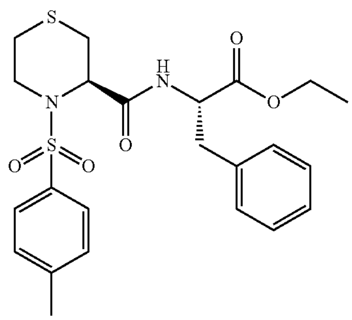 [SMILES: CCOC(=O)[C@H](Cc1ccccc1)NC(=O)[C@@H]1CSCCN1S(=O)(=O)c1ccc(C)cc1] | (S)-ethyl-3-phenyl-2((R)-(4-methyl-phenyl)sulfonyltetrahydro-1,4-thiazin-3-aminoformyl)propionate |
| 18 | 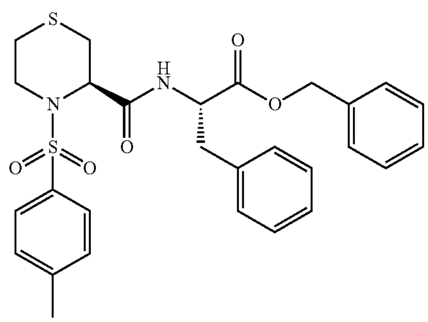 [SMILES: Cc1ccc(S(=O)(=O)N2CCSC[C@H]2C(=O)N[C@@H](Cc2ccccc2)C(=O)OCc2ccccc2)cc1] | (S)-benzyl-3-phenyl-2((R)-(4-methyl-phenyl)sulfonyltetrahydro-1,4-thiazin-3-aminoformyl)propionate |
| 19 | 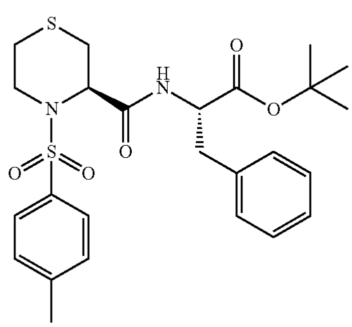 [SMILES: Cc1ccc(S(=O)(=O)N2CCSC[C@H]2C(=O)N[C@@H](Cc2ccccc2)C(=O)OC(C)(C)C)cc1] | (S)-tert-butyl-3-phenyl-2((R)-(4-methylphenyl)sulfonyltetrahydro-1,4-thiazin-3-aminoformyl)propionate |
| 20 | 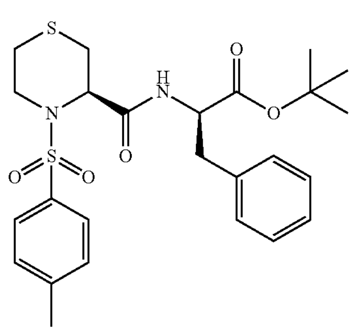 [SMILES: Cc1ccc(S(=O)(=O)N2CCSC[C@H]2C(=O)N[C@H](Cc2ccccc2)C(=O)OC(C)(C)C)cc1] | (R)-tert-butyl-3-phenyl-2((R)-(4-methylphenyl)sulfonyltetrahydro-1,4-thiazin-3-aminoformyl)propionate |

| Compound No. | Structure | Name |
|---|---|---|
| 21 | 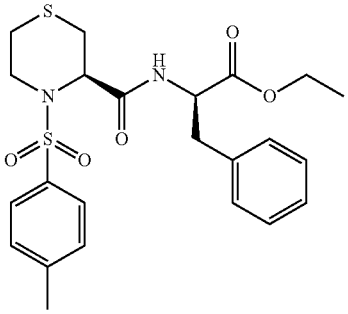 [SMILES: CCOC(=O)[C@@H](Cc1ccccc1)NC(=O)[C@@H]1CSCCN1S(=O)(=O)c1ccc(C)cc1] | (R)-ethyl-3-phenyl-2((R)-(4-methyl-phenyl)sulfonyltetrahydro-1,4-thiazin-3-aminoformyl)propionate |
| 22 | 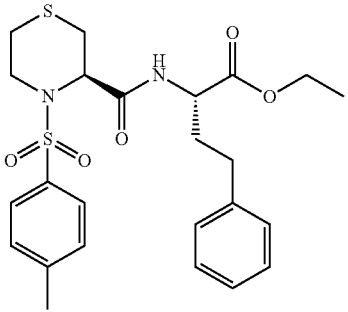 [SMILES: CCOC(=O)[C@H](CCc1ccccc1)NC(=O)[C@@H]1CSCCN1S(=O)(=O)c1ccc(C)cc1] | (S)-ethyl-4-phenyl-2((R)-(4-methyl-phenyl)sulfonyltetrahydro-1,4-thiazin-3-aminoformyl)butyrate |
| 23 | 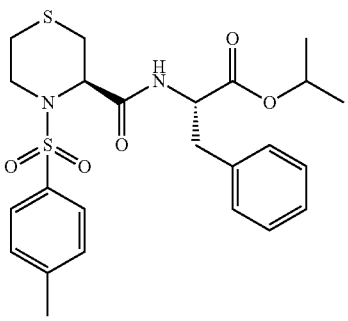 [SMILES: Cc1ccc(S(=O)(=O)N2CCSC[C@H]2C(=O)N[C@@H](Cc2ccccc2)C(=O)OC(C)C)cc1] | (S)-isopropyl-3-phenyl-2((R)-(4-methylphenyl)sulfonyltetrahydro-1,4-thiazin-3-aminoformyl)propionate |
| 24 | 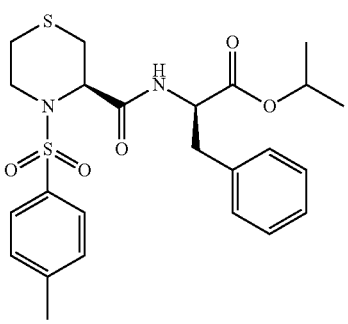 [SMILES: Cc1ccc(S(=O)(=O)N2CCSC[C@H]2C(=O)N[C@H](Cc2ccccc2)C(=O)OC(C)C)cc1] | (R)-isopropyl-3-phenyl-2((R)-(4-methylphenyl)sulfonyltetrahydro-1,4-thiazin-3-aminoformyl)propionate |

| Compound No. | Structure | Name |
|---|---|---|
| 25 | 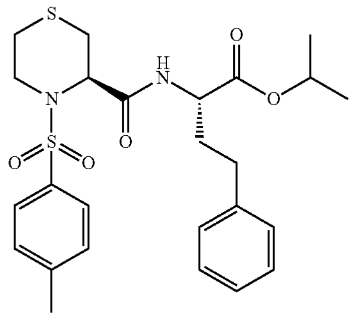 [SMILES: Cc1ccc(S(=O)(=O)N2CCSC[C@H]2C(=O)N[C@@H](CCc2ccccc2)C(=O)OC(C)C)cc1] | (S)-isopropyl-4-phenyl-2((R)-(4-methylphenyl)sulfonyltetrahydro-1,4-thiazin-3-aminoformyl)butyrate |
| 26 | 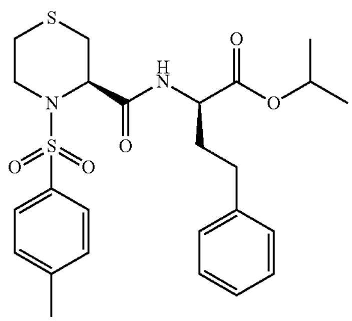 [SMILES: Cc1ccc(S(=O)(=O)N2CCSC[C@H]2C(=O)N[C@H](CCc2ccccc2)C(=O)OC(C)C)cc1] | (R)-isopropyl-4-phenyl-2((R)-(4-methylphenyl)sulfonyltetrahydro-1,4-thiazin-3-aminoformyl)butyrate |
| 28 | 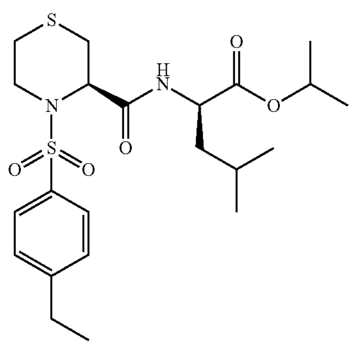 [SMILES: CCc1ccc(S(=O)(=O)N2CCSC[C@H]2C(=O)N[C@H](CC(C)C)C(=O)OC(C)C)cc1] | (3R)-4-[(4-ethylbenzenesulfonyl)]tetrahydro-1,4-thiazin-3-carbonyl-L-leucine isopropyl ester |

In another aspect, the invention provides a pharmaceutical composition, comprising the compound as defined in any of the aspects above, or a pharmaceutically acceptable salt or solvate thereof; preferably, the composition further comprises one or more pharmaceutically acceptable carrier(s) and/or excipient(s). The carrier and/or excipient includes, but is not limited to, ion exchanger, aluminum oxide, aluminum stearate, lecithin, serum protein such as human serum protein; buffer substance such as phosphate, glycerol, sorbic acid, potassium sorbate, a partial glyceride mixture of saturated plant fatty acid, water, salt, or electrolyte, such as protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethylcellulose sodium, polyacrylic ester, beewax, polyethylene-polyoxypropylene block copolymer, and lanolin.

The pharmaceutical composition may be prepared in any pharmaceutically acceptable form. The pharmaceutical composition may be administered to a patient or subject in need thereof by any suitable route, such as orally, parenterally, rectally, or intrapulmonarily, etc. When administered orally, the pharmaceutical composition may be prepared into a conventional solid formulation, such as tablet, capsule, pill, and granule; or may be prepared into an oral liquid formulation, such as oral solution, oral suspension, and syrup. When the pharmaceutical composition is prepared into an oral formulation, suitable fillers, binding agents, disintegrating agents, lubricants and the like may be added. When administered parenterally, the pharmaceutical composition may be prepared into an injection, including injection, sterile powder for injection and concentrated solution for injection. When the pharmaceutical composition is prepared into an injection, a conventional method existing in the pharmaceutical field may be used. When preparing an injection, additives may not be added, or a suitable additive is added depending on the property of drug. When administered rectally, the pharmaceutical composition may be prepared into a suppository, etc. When administered intrapulmonarily, the pharmaceutical composition may be prepared into an inhalant, or spraying agent, etc.

In another aspect, the invention provides a use of the compound or a pharmaceutically acceptable salt or solvate thereof as defined in any of the aspects above in the manufacture of a medicament for preventing and/or treating a neurodegenerative disease, a neuropathy caused by a physical trauma, or a neuropathy caused by a related disease in a subject;

preferably, the neurodegenerative disease is selected from the group consisting of Alzheimer's disease, Parkinson's disease, Huntington's disease, amyotrophic lateral sclerosis and marrowbrain multiple sclerosis;

preferably, the physical trauma is selected from the group consisting of heat injury, cold injury, mechanical injury and electric injury;

preferably, the related disease is selected from the group consisting of acquired immunodeficiency, diabetes mellitus and stroke;

preferably, the subject is a mammal, such as bovine, equine, caprid, suidae, canine, feline, rodent, and primate; preferably, the subject is human.

In another aspect, the invention provides a method for preventing and/or treating a neurodegenerative disease, a neuropathy caused by a physical trauma, or a neuropathy caused by a related disease in a subject, comprising administering a therapeutically and/or prophylactically effective amount of the compound, or a pharmaceutically acceptable salt or solvate thereof as defined in any of the aspects above, or the pharmaceutical composition as defined above, to a subject in need thereof.

Preferably, the neurodegenerative disease is selected from the group consisting of Alzheimer's disease, Parkinson's disease, Huntington's disease, amyotrophic lateral sclerosis and marrowbrain multiple sclerosis;

preferably, the physical trauma is selected from the group consisting of heat injury, cold injury, mechanical injury and electric injury;

preferably, the related disease is selected from the group consisting of acquired immunodeficiency, diabetes mellitus and stroke;

preferably, the subject is a mammal, such as bovine, equine, caprid, suidae, canine, feline, rodent, and primate; preferably, the subject is human.

In another aspect, the invention provides the compound as defined in any of the aspects above, or a pharmaceutically acceptable salt or solvate thereof, for use in prevention and/or treatment of a neurodegenerative disease, a neuropathy caused by a physical trauma, or a neuropathy caused by a related disease in a subject;

preferably, the neurodegenerative disease is selected from the group consisting of Alzheimer's disease, Parkinson's disease, Huntington's disease, amyotrophic lateral sclerosis and marrowbrain multiple sclerosis;

preferably, the physical trauma is selected from the group consisting of heat injury, cold injury, mechanical injury and electric injury;

preferably, the related disease is selected from the group consisting of acquired immunodeficiency, diabetes mellitus and stroke;

preferably, the subject is a mammal, such as bovine, equine, caprid, suidae, canine, feline, rodent, and primate; preferably, the subject is human.

The invention further provides a method for the preparation of a compound of formula (I), the scheme of which is as follows:

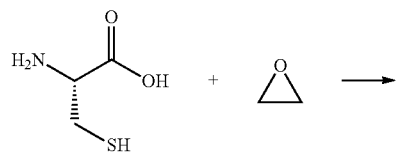

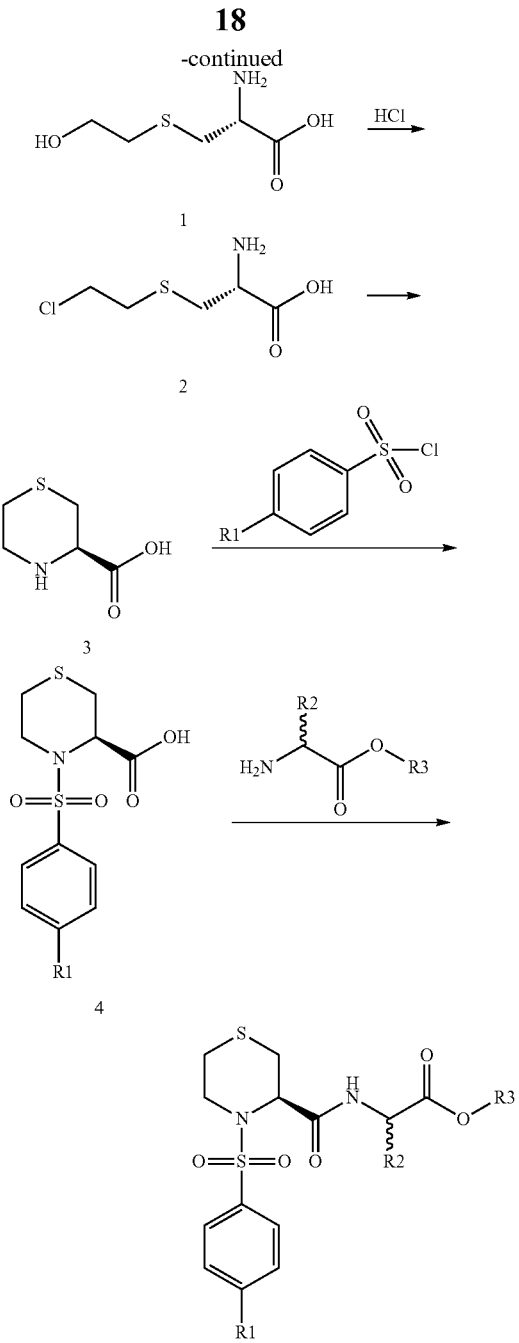

wherein, R1, R2, and R3 have the same meanings as defined above.

In the preparation, substances represented by abbreviations are as follows: DCC: dicyclohexylcarbodiimide; DMAP: 4-dimethylaminopyridine; DCM: dichloromethane; THF: tetrahydrofuran.

The exemplary steps of the preparation are as follows:

(1) L-cysteine is dissolved in a polar solvent (e.g., water), pH is adjusted to 7.0, ethylene oxide is added dropwise at 0-10° C., and the reaction is carried out to obtain Compound 1.

(2) Compound 1 is dissolved in concentrated hydrochloric acid, and the reaction is carried out at 90-95° C. to obtain Compound 2.

(3) Compound 2 is dissolved in water, and an alkaline solution (e.g., a sodium bicarbonate aqueous solution) is added dropwise; after extraction, drying and concentration, the organic phase is obtained. A polar solvent (e.g., methanol) is added, and the reaction is carried out at room temperature to obtain Compound 3.

(4) Compound 3 is dissolved in a polar solvent (e.g., THF); an alkaline solution (e.g., a sodium bicarbonate aqueous solution) and Raw material 1 are added, and the reaction is carried out at room temperature to obtain Compound 4; the Raw material 1 is preferably the benzenesulfonyl chloride substituted with R1 as shown in the scheme above.

(5) Compound 4 and Raw material 2 are reacted in the presence of a dehydrating agent (e.g., DCC), a catalyst (e.g., DMAP) and a base (e.g., triethylamine), to obtain the target product; the Raw material 2 is preferably the amino acid ester containing the groups R2 and R3 as shown in the scheme above, or a salt thereof, such as a hydrochlorate thereof.

Beneficial Effects of the Invention

As compared to the prior art, the compounds of Formula (I) according to the invention have one or more of the following beneficial effects:

(1) the compound of the invention has the neurotrophic activity improved relative to the existing thiazideamide derivative;

(2) the compound of the invention is superior to the existing thiazideamide derivative in terms of the in vivo efficacy in mice with apoplexy; and (3) the compound of the invention is superior to the existing thiazideamide derivative in terms of the ability of passing through blood-brain barrier.

The compounds of the invention can be used to prevent and/or treat a neurodegenerative disease, such as Alzheimer's disease, Parkinson's disease, Huntington's disease, amyotrophic lateral sclerosis and marrowbrain multiple sclerosis; and a neuropathy caused by a physical trauma or a related disease, such as acquired immunodeficiency, diabetes mellitus and stroke.

SPECIFIC MODES FOR CARRYING OUT THE INVENTION

The embodiments of the invention are described by combining the following examples. However, a person skilled in the art understands that the following examples are only intended to describe the invention, and shall not be regarded as defining the scope of the invention. In the case where the concrete conditions are not indicated in the examples, the examples are carried out according to conventional conditions or the conditions recommended by the manufacturer. The reagents or apparatuses, the manufacturers of which are not indicated, are the conventional products that are commercially available.

Reagents: raw materials, the synthetic processes of which are not provided, are commercially available, and solvents for reactions have been subjected to standard pretreatment.

Apparatus: the melting point of a compound is determined by RY-1 Melting Point Tester; $^1$H NMR is determined by ARX-400 NMR instrument; mass spectrum is determined by VG-ZabSpec MS instrument.

Example 1 Synthesis of 2-hydroxyethylcysteine (Compound 1)

To a 2000 ml round bottom flask, 109 g (0.9 mol) L-cysteine was added, dissolved in 1000 ml distilled water and cooled to 10° C. in an ice bath. 24 ml 1M NaOH aqueous solution was added to neutralize the solution to a pH of about 7. At 10° C., the pre-cooled ethylene oxide (100 ml) was pipetted and added. The reaction was then carried out at a constant temperature of 10° C. for 1 h, and then at room temperature for 1.5 h.

The resultant mixture was extracted with diethyl ether (400 ml×4) to remove the unreacted ethylene oxide. At a temperature below 60° C., the water phase was removed from the system by distillation, to obtain a yellow solid. After recrystallization with a mixed solvent (water:ethanol=85 ml: 350 ml) and filtration, the solid was sufficiently washed with 95 wt % ethanol, to obtain the product, as a white scale-like solid (about 100 g, yield: 67.5%).

m.p. 195-196° C. $^1$H-NMR (400 MHz, D$_2$O) δ: 3.96131 (dd, 1H, J$_1$=4.272 Hz, J$_2$=7.816 Hz), 3.80680-3.77293 (m, 2H), 3.17887 (dd, 1H, J$_1$=4.268 Hz, J$_2$=14.814 Hz), 3.08224 (dd, 1H, J$_1$=7.480 Hz, J$_2$=14.814 Hz), 2.80103 (t, 2H, J=6.036 Hz).

Example 2 Synthesis of 2-chloroethylcysteine hydrochlorate (Compound 2)

To a 1000 ml round bottom flask, 44 g 2-hydroxyethylcysteine was added, and dissolved in 600 ml concentrated hydrochloric acid. The mixture was heated to 90-95° C., and reacted under stirring for 7 h. After the reaction, the resultant mixture was stored in a refrigerator and was on standing overnight. A large amount of needle-like solid was precipitated from the system. The solvent was removed by suction filtration, and the solid obtained was dried in air, to obtain the product, as an off-white solid (about 40 g, yield: >70%).

m.p. 185-186° C. $^1$H-NMR (400 MHz, D$_2$O) δ: 4.30477-4.26952 (m, 1H), 3.81913-3.78409 (m, 2H), 3.25903 (dd, 1H, J$_1$=4.444 Hz, J$_2$=14.984 Hz), 3.18877 (dd, 1H, J$_1$=7.352 Hz, J$_2$=15.072 Hz), 3.04410-3.00625 (m, 2H).

Example 3 Synthesis of L-1,4-thiazin-3-carboxylic acid hydrochlorate (Compound 3)

20 g 2-chloroethyl cysteine hydrochlorate was dissolved in water, and 7.2 g NaHCO$_3$ aqueous solution was added dropwisely in an ice bath. After the addition, the solution was stirred well to carry out neutralization. After extraction with ethyl acetate for three times, the organic phases were combined, and dried with Na$_2$SO$_4$. The solvent was removed by distillation at reduced pressure, and 400 ml anhydrous methanol was then added. The reaction was carried out at room temperature for 5 days. The solvent was removed by distillation at reduced pressure, and recrystallization was carried out using a mixed solvent (methanol-diethyl ether), to obtain a subalbous solid (about 6 g). Specific rotation $[\alpha]_D^{24.5}$=−27.1° (H$_2$O).

m.p.>230° C. $^1$H-NMR (400 MHz, CDCl$_3$) δ: 3.67672-3.64308 (m, 1H), 3.55044-3.50108 (m, 1H), 3.16622-3.08322 (m, 1H), 2.92045-2.90326 (m, 1H), 2.83678-2.75406 (m, 2H), 2.61390-2.59272 (m, 1H). MS (FAB) m/z: 148.

Example 4 Synthesis of L-4-p-toluenesulfonyl-1,4-thiazin-3-carboxylic Acid (Compound 4)

2.3 g (15.7 mmol) L-1,4-thiazin-3-carboxylic acid hydrochlorate was dissolved in 17 ml THF, 77 ml 10 wt % NaHCO$_3$ aqueous solution was added, and 17 ml THF solution comprising 2.90 g (15.2 mmol) p-toluenesulfonyl chloride was added dropwise. The mixture was stirred at room temperature for 19-24 h. After the reaction, hydrochloric acid was added to adjust pH value to 1-2, and ethyl acetate (10 ml×3) was used for extraction. The supernatant solution was dried with anhydrous magnesium sulfate. The solvent was removed by suction filtration and rotary evaporation, so as to obtain a brown oil. Recrystallization was carried out using a mixed solvent of ethyl acetate and cyclohexane, to obtain a white crystal (4.3 g, yield: 93.5%). m.p. 66° C. (decomposition). specific rotation $[\alpha]_D^{24.5}$= −81.6° (H$_2$O).

$^1$H-NMR (400 MHz, CDCl$_3$) δ: 7.68268-7.66234 (d, 2H), 7.30642-7.26434 (m, 2H), 5.12406-5.10728 (m, 1H), 4.03322-3.99196 (m, 1H), 3.46642-3.40848 (m, 1H), 3.02301-2.99292 (m, 2H), 2.76875-2.73724 (m, 1H), 2.42688 (s, 3H), 2.38062 (s, 1H). MS (FAB) m/z: 301.2.

Example 5 Synthesis of (3R)-4-[(4-methylbenzenesulfonyl)]-1,4-thiazin-3-carbonyl-L-leucine ethyl ester (Compound 5, ZL01142744.2)

4.2 g (0.14 mol) L-4-p-toluenesulfonyl-1,4-thiazin-3-carboxylic acid, 3.0 g (0.017 mmol) L-leucine ethyl ester hydrochlorate (Raw material 2), 3.2 g (0.014 mol) DCC and 1.7 g (0.014 mol) DMAP were dissolved in 200 ml dichloromethane, and 6 ml (0.042 mol) triethylamine was added. The reaction was carried out at room temperature for 24 h. The solid was removed by filtration, and the solvent was removed by distillation. The residue was dissolved in a suitable amount of ethyl acetate. The insoluble substance was removed by filtration, and the resultant mixture was diluted with ethyl acetate. The resultant solution was washed sequentially with 10% NaHCO$_3$ solution and saturated NaCl solution, and dried with anhydrous Na$_2$SO$_4$. The drying agent was removed, and a part of ethyl acetate was removed by distillation. Separation was carried out using flash chromatography column (the eluant was DCM:CH$_3$Cl=1:1), to obtain an oil 4.0 g. Specific rotation $[\alpha]_D^{24.5}$=−110.1° (c 2.00, DCM).

$^1$H-NMR (400 MHz, CDCl$_3$) δ: 7.77237-7.74077 (m, 2H), 7.36382 (d, 2H, J=−7.988 Hz), 6.74090 (d, 1H, J=9.244 Hz), 4.80098-4.77466 (m, 1H), 4.68244-4.58898 (m, 1H), 4.28174-4.15708 (m, 3H), 3.53789-3.28674 (m, 1H), 3.13092 (d, 1H, J=13.676), 2.56954-2.42247 (m, 5H), 2.24620-2.20545 (m, 1H), 1.66352-1.53450 (m, 3H), 1.30702-1.26745 (m, 3H), 0.96159-0.91891 (m, 6H). MS (EI) m/z: 443.4, 397.2, 369.2, 263.1, 256.1, 155.0, 139.2, 101.1.

Example 6 Synthesis of (3R)-4-[(4-methylbenzenesulfonyl)]-1,4-thiazin-3-carbonyl-D-leucine isopropyl ester (Compound 6, CN102675244)

(3R)-4-[(4-methylbenzenesulfonyl)]-1,4-thiazin-3-carbonyl-D-leucine isopropyl ester was prepared in accordance with the steps in Example 5, by using D-leucine isopropyl ester hydrochlorate as Raw material 2, wherein the product was a white crystal (yield: 91.5%). Specific rotation $[\alpha]_D^{24.5}$=−103.7°.

m.p. 81-83° C. $^1$H-NMR (400 MHz, CDCl$_3$) δ: 7.76237-7.74077 (d, 2H J=8.208 Hz), 7.37382-7.26511 (d, 2H, J=8.208 Hz), 6.75090 (d, 1H, J=8.944 Hz), 5.40112 (m, 1H), 4.79298-4.25166 (m, 3H), 3.54989-3.53674 (t, 1H, J=12.31110), 3.15292-3.11800 (d, 1H, J=13.676 HZ), 2.56054-2.46247 (m, 4H), 2.23220-2.20345 (m, 1H), 1.62552-1.43450 (m, 4H), 1.26202-1.24745 (m, 6H), 0.94659-0.93191 (m, 6H). MS (EI) m/z: 457.3, 397.2, 369.2, 256.2, 154.7, 101.1.

Example 7 Synthesis of (2S,3R)-ethyl-3-methyl-2 ((R)-(4-methylphenyl)sulfonylthiazine-3-aminoformyl)valerate (Compound 7)

(2S,3R)-ethyl-3-methyl-2((R)-(4-methylphenyl)sulfonylthiazine-3-aminoformyl)valerate was prepared in accordance with the steps in Example 5, by using L-isoleucine ethyl ester hydrochlorate (1.45 g) as Raw material 2, wherein the product was a white solid (yield: 65%).

m.p. 88-90° C. $^1$H-NMR (400 MHz, CDCl$_3$) δ: 7.76 (2H, d, J=8.42 Hz), 7.37 (2H, d, J=8.41 Hz), 7.01 (1H, d, J=8.64 Hz), 4.79 (1H, t, J=2.82 Hz), 4.58 (1H, m), 4.20 (3H, m), 3.66 (1H, t, J=2.43 Hz), 3.34 (1H, d, J=13.71 Hz), 3.13 (1H, d, J=11.86 Hz), 2.56-0.93 (14H, m). MS-EI (m/z): 443.1669 [M+H]+.

Example 8 Synthesis of (2S,3R)-methyl-3-methyl-2 ((R)-(4-methylphenyl)sulfonylthiazine-3-aminoformyl)valerate (Compound 8)

The product (1.52 g, yield: 71%) as a white solid was prepared in accordance with the steps in Example 5, by using 1.02 g (7 mmol) L-isoleucine methyl ester as Raw material 2.

m.p. 92-94° C. $^1$H-NMR (400 MHz, CDCl$_3$) δ: 7.76 (2H, d, J=8.42 Hz), 7.37 (2H, d, J=8.41 Hz), 7.01 (1H, d, J=8.64 Hz), 4.81 (1H, t, J=3.14 Hz), 4.58 (1H, m), 4.20 (1H, m), 3.75 (3H, m), 3.33 (1H, t, J=2.60 Hz), 3.11 (1H, d, J=11.82 Hz), 2.57-0.93 (15H, m). MS-EI (m/z): 429.1512[M+H]+.

Example 9 Synthesis of (2S,3R)-tert-butyl-3-methyl-2((R)-(4-methylphenyl)sulfonylthiazine-3-aminoformyl)valerate (Compound 9)

The product (1.53 g, yield: 65%) as a white solid was prepared in accordance with the steps in Example 5, by using 1.31 g (7 mmol) L-isoleucine tert-butyl ester as Raw material 2.

m.p. 80-82° C. $^1$H-NMR (400 MHz, CDCl$_3$) δ: 7.76 (2H, d, J=8.41 Hz), 7.37 (2H, d, J=−8.40 Hz), 7.01 (1H, d, J=8.67 Hz), 4.78 (1H, t, J=3.40 Hz), 4.47 (1H, m), 4.25 (1H, t, J=5.20 Hz), 3.44 (1H, t, J=12.43 Hz), 3.13 (1H, d, J=13.72 Hz), 2.60-0.93 (24H, m). MS-EI (m/z): 471.1982[M+H]+.

Example 10 Synthesis of (S)-methyl-3-methyl-2 ((R)-(4-methylphenyl)sulfonylthiazine-3-aminoformyl)butyrate (Compound 10)

The product (1.26 g, yield: 61%) as a white solid was prepared in accordance with the steps in Example 5, by using 0.91 g (7 mmol) L-valine methyl ester as Raw material 2.

m.p. 93-95° C. $^1$H-NMR (400 MHz, CDCl$_3$) δ: 7.76 (2H, d, J=8.43 Hz), 7.37 (2H, d, J=8.43 Hz), 7.01 (1H, d, J=8.62 Hz), 4.81 (1H, t, J=3.40 Hz), 4.58 (1H, m), 4.20 (1H, m), 3.75 (3H, m), 3.33 (1H, t, J=2.60 Hz), 3.11 (1H, d, J=11.82 Hz), 2.60-0.92 (13H, m). MS-EI (m/z): 415.1356 [M+H]+.

Example 11 Synthesis of (S)-benzyl-3-methyl-2 ((R)-(4-methylphenyl)sulfonylthiazine-3-aminoformyl)butyrate (Compound 11)

The product (1.64 g, yield: 67%) as a white solid was prepared in accordance with the steps in Example 5, by using 1.44 g (7 mmol) L-valine benzyl ester as Raw material 2.

m.p. 85-87° C. ¹H-NMR (400 MHz, CDCl₃) δ: 7.76 (2H, d, J=8.41 Hz), 7.37 (2H, d, J=8.43 Hz), 7.34 (4H, m), 7.01 (1H, d, J=8.62 Hz), 5.20 (2H, dd), 4.82 (1H, t, J=3.40 Hz), 4.56 (1H, d, J=12.31 Hz), 4.19 (1H, m), 3.34 (1H, d, J=12.63 Hz), 3.14 (1H, d, J=13.76 Hz), 2.56-0.80 (13H, m). MS-EI (m/z): 491.1669[M+H]+.

Example 12 Synthesis of (S)-tert-butyl-3-methyl-2 ((R)-(4-methylphenyl)sulfonylthiazine-3-aminoformyl)butyrate (Compound 12)

The product (1.65 g, yield: 71%) as a white solid was prepared in accordance with the steps in Example 5, by using 1.20 g (7 mmol) L-valine tert-butyl ester as Raw material 2.
m.p. 90-92° C. ¹H-NMR (400 MHz, CDCl₃) δ: 7.76 (2H, d, J=8.42 Hz), 7.37 (2H, d, J=8.41 Hz), 7.01 (1H, d, J=8.65 Hz), 4.78 (1H, t, J=3.40 Hz), 4.44 (1H, m), 4.25 (1H, t, J=5.20 Hz), 3.36 (1H, m), 3.17 (1H, d, J=13.34 Hz), 2.59-0.89 (22H, m). MS-EI (m/z): 457.1825[M+H]+.

Example 13 Synthesis of (S)-ethyl-3-methyl-2((R)-(4-methylphenyl)sulfonylthiazine-3-aminoformyl) butyrate (Compound 13)

The product (1.46 g, yield: 68%) as a white solid was obtained in accordance with the steps in Example 5, by using 1.01 g (7 mmol) L-valine ethyl ester as Raw material 2.
m.p. 87-89° C. ¹H-NMR (400 MHz, CDCl₃) δ: 7.76 (2H, d, J=8.42 Hz), 7.37 (2H, d, J=8.44 Hz), 7.01 (1H, d, J=8.64 Hz), 4.80 (1H, t, J=3.40 Hz), 4.54 (1H, m), 4.21 (3H, m), 3.48 (1H, t, J=12.31 Hz), 3.13 (1H, d, J=12.52 Hz), 2.59-0.88 (16H, m). MS-EI (m/z): 429.1512[M+H]+.

Example 14 Synthesis of (R)-methyl-3-methyl-2 ((R)-(4-methylphenyl)sulfonylthiazine-3-aminoformyl)butyrate (Compound 14)

The product (1.43 g, yield: 69%) as a white solid was obtained in accordance with the steps in Example 5, by using 0.91 g (7 mmol) D-valine methyl ester as Raw material 2.
m.p. 90-92° C. ¹H-NMR (400 MHz, CDCl₃) δ: 7.76 (2H, d, J=8.42 Hz), 7.37 (2H, d, J=8.41 Hz), 7.01 (1H, d, J=8.65 Hz), 4.80 (1H, t, J=3.40 Hz), 4.59 (1H, m), 4.24 (1H, d, J=12.52 Hz), 3.75 (3H, m), 3.44 (1H, t, J=12.33 Hz), 3.15 (1H, d, J=13.75 Hz), 2.59-0.84 (13H, m). MS-EI (m/z): 415.1356[M+H]+.

Example 15 Synthesis of (R)-tert-butyl-3-methyl-2 ((R)-(4-methylphenyl)sulfonylthiazine-3-aminoformyl)butyrate (Compound 15)

The product (1.51 g, yield: 66%) as a white solid was obtained in accordance with the steps in Example 5, by using 1.21 g (7 mmol) D-valine tert-butyl ester as Raw material 2.
m.p. 88-90° C. ¹H-NMR (400 MHz, CDCl₃) δ: 7.76 (2H, d, J=8.12 Hz), 7.36 (2H, d, J=8.41 Hz), 6.91 (1H, d, J=8.35 Hz), 4.80 (1H, t, J=3.40 Hz), 4.48 (1H, m), 4.23 (1H, d, J=12.32 Hz), 3.50 (1H, t, J=−11.95 Hz), 3.13 (1H, d, J=13.74 Hz), 2.59-0.83 (22H, m). MS-EI (m/z): 457.1825 [M+H]+.

Example 16 Synthesis of (S)-methyl-3-phenyl-2 ((R)-(4-methylphenyl)sulfonylthiazine-3-aminoformyl)propionate (Compound 16)

The product (1.55 g, yield: 67%) as a white solid was obtained in accordance with the steps in Example 5, by using 1.25 g (7 mmol) L-phenylalanine methyl ester as Raw material 2.

m.p. 85-98° C. ¹H-NMR (400 MHz, CDCl₃) δ: 7.69 (2H, d, J=8.42 Hz), 7.30 (5H, m), 7.15 (2H, d, J=8.41 Hz), 6.86 (1H, d, J=8.62 Hz), 4.80 (1H, t, J=3.40 Hz), 4.10 (1H, m), 3.75 (3H, m), 3.29 (1H, t), 3.07 (2H, d), 2.65-0.88 (8H, m). MS-EI (m/z): 463.1356[M+H]+.

Example 17 Synthesis of (S)-ethyl-3-phenyl-2((R)-(4-methylphenyl)sulfonylthiazine-3-aminoformyl) propionate (Compound 17)

The product (1.65 g, yield: 69%) as a white solid was obtained in accordance with the steps in Example 5, by using 1.35 g (7 mmol) L-phenylalanine ethyl ester as Raw material 2.
m.p. 91-93° C. ¹H-NMR (400 MHz, CDCl₃) δ: 7.69 (2H, d, J=8.42 Hz), 7.30 (5H, m), 7.16 (2H, d, J=8.41 Hz), 6.88 (1H, d, J=8.63 Hz), 4.77 (2H, m), 4.22 (2H, m), 3.89 (1H, m), 3.29 (1H, m), 3.08 (2H, m), 2.69-0.91 (10H, m). MS-EI (m/z): 477.1512 [M+H]+.

Example 18 Synthesis of (S)-benzyl-3-phenyl-2 ((R)-(4-methylphenyl)sulfonylthiazine-3-aminoformyl)propionate (Compound 18)

The product (1.70 g, yield: 63%) as a white solid was obtained in accordance with the steps in Example 5, by using 1.79 g (7 mmol) L-phenylalanine benzyl ester as Raw material 2.
m.p. 88-90° C. ¹H-NMR (400 MHz, CDCl₃) δ: 7.67 (2H, d, J=8.32 Hz), 7.41 (5H, m), 7.30 (3H, m), 7.19 (2H, d, J=8.42 Hz), 7.06 (2H, m), 6.87 (1H, d, J=8.01 Hz), 5.21 (2H, dd, J=3.60 Hz), 4.84 (1H, m), 4.72 (1H, t, J=3.10 Hz), 3.92 (1H, m), 3.31 (1H, d, J=12.15 Hz), 3.04 (2H, d, J=11.66 Hz), 2.75-0.94 (7H, m). MS-EI (m/z): 539.1669[M+H]+.

Example 19 Synthesis of (S)-tert-butyl-3-phenyl-2 ((R)-(4-methylphenyl)sulfonylthiazine-3-aminoformyl)propionate (Compound 19)

The product (1.72 g, yield: 68%) as a white solid was obtained in accordance with the steps in Example 5, by using 1.55 g (7 mmol) L-phenylalanine tert-butyl ester as Raw material 2.
m.p. 92-94° C. ¹H-NMR (400 MHz, CDCl₃) δ: 7.72 (2H, d, J=8.32 Hz), 7.32 (2H, d, J=8.13 Hz), 7.22 (5H, m), 6.88 (1H, d, J=8.10 Hz), 4.68 (1H, t, J=6.40 Hz), 3.96 (1H, m), 3.26 (1H, m), 3.08 (2H, d, J=12.30 Hz), 2.78 (1H, d, =19.34 Hz), 2.57-0.94 (16H, m). MS-EI (m/z): 505.1825 [M+H]+.

Example 20 Synthesis of (R)-tert-butyl-3-phenyl-2 ((R)-(4-methylphenyl)sulfonylthiazine-3-aminoformyl)propionate (Compound 20)

The product (1.59 g, yield: 63%) as a white solid was obtained in accordance with the steps in Example 5, by using 1.55 g (7 mmol) D-phenylalanine tert-butyl ester as Raw material 2.
m.p. 88-92° C. ¹H-NMR (400 MHz, CDCl₃) δ: 7.70 (2H, d, J=8.21 Hz), 7.33 (5H, m), 7.25 (2H, d, J=8.13 Hz), 6.97 (1H, d, J=8.15 Hz), 4.79 (1H, t, J=6.40 Hz), 4.11 (1H, m), 3.38 (1H, t, J=12.30 Hz), 3.10 (2H, m), 3.07 (1H, d, J=19.36 Hz), 2.57-0.94 (16H, m). MS-EI (m/z): 505.1825 [M+H]+.

Example 21 Synthesis of (R)-ethyl-3-phenyl-2((R)-(4-methylphenyl)sulfonylthiazine-3-aminoformyl)propionate (Compound 21)

The product (1.65 g, yield: 69%) as a white solid was obtained in accordance with the steps in Example 5, by using 1.35 g (7 mmol) D-phenylalanine ethyl ester as Raw material 2.

m.p. 86-89° C. $^1$H-NMR (400 MHz, CDCl$_3$) δ: 7.69 (2H, d, J=8.43 Hz), 7.33 (5H, m), 7.27 (2H, d, J=8.42 Hz), 7.13 (1H, d, J=8.31 Hz), 4.94 (1H, m), 4.80 (1H, m), 4.12 (2H, m), 3.73 (2H, d, J=12.33 Hz), 3.21 (1H, t, J=11.96 Hz), 3.10 (3H, m), 2.56-0.94 (8H, m). MS-EI (m/z): 463.1356 [M+H]+.

Example 22 Synthesis of (S)-ethyl-4-phenyl-2((R)-(4-methylphenyl)sulfonylthiazine-3-aminoformyl)butyrate (Compound 22)

The product (1.64 g, yield: 67%) as a white solid was obtained in accordance with the steps in Example 5, by using 1.45 g (7 mmol) L-homophenylalanine ethyl ester as Raw material 2.

m.p. 87-89° C. $^1$H-NMR (400 MHz, CDCl$_3$) δ: 7.76 (2H, d, J=8.44 Hz), 7.33 (5H, m), 7.25 (2H, d, J=8.12 Hz), 7.16 (1H, d, J=8.31 Hz), 4.85 (1H, m), 4.62 (1H, m), 4.19 (2H, d, J=19.33 Hz), 4.02 (1H, m), 3.43 (1H, d), 3.11 (1H, m), 2.55-0.94 (13H, m). MS-EI (m/z): 491.1669[M+H]+.

Example 23 Synthesis of (S)-isopropyl-3-phenyl-2((R)-(4-methylphenyl)sulfonylthiazine-3-aminoformyl)propionate (Compound 23)

The product (1.65 g, yield: 67%) as a white solid was obtained in accordance with the steps in Example 5, by using 1.45 g (7 mmol) L-phenylalanine isopropyl ester as Raw material 2.

m.p. 85-87° C. $^1$H-NMR (400 MHz, CDCl$_3$) δ: 7.69 (2H, d, J=8.46 Hz), 7.31 (5H, m), 7.17 (2H, d, J=8.46 Hz), 6.90 (1H, d, J=8.34 Hz), 5.01 (1H, t, J=6.40 Hz), 4.74 (1H, m), 4.12 (1H, m), 4.08 (1H, m), 3.28 (1H, t, J=12.3 Hz), 3.08 (2H, d, J=−19.33 Hz), 2.50-0.94 (13H, m). MS-EI (m/z): 491.1669 [M+H]+.

Example 24 Synthesis of (R)-isopropyl-3-phenyl-2((R)-(4-methylphenyl)sulfonylthiazine-3-aminoformyl)propionate (Compound 24)

The product (1.60 g, yield: 65%) as a white solid was obtained in accordance with the steps in Example 5, by using 1.45 g (7 mmol) D-phenylalanine isopropyl ester as Raw material 2.

m.p. 86-89° C. $^1$H-NMR (400 MHz, CDCl$_3$) δ: 7.70 (2H, d, J=8.42 Hz), 7.32 (5H, m), 7.18 (2H, d, J=8.41 Hz), 6.92 (1H, d, J=8.33 Hz), 5.01 (1H, t, J=6.40 Hz), 4.82 (1H, m), 4.11 (2H, m), 3.35 (1H, t, J=12.43 Hz), 3.09 (2H, d, J=12.12 Hz), 2.50-0.92 (13H, m). MS-EI (m/z): 491.1669 [M+H]+.

Example 25 Synthesis of (S)-isopropyl-4-phenyl-2((R)-(4-methylphenyl)sulfonylthiazine-3-aminoformyl)butyrate (Compound 25)

The product (1.67 g, yield: 66%) as a white solid was obtained in accordance with the steps in Example 5, by using 1.55 g (7 mmol) L-homophenylalanine isopropyl ester as Raw material 2.

m.p. 87-89° C. $^1$H-NMR (400 MHz, CDCl$_3$) δ: 7.75 (2H, d, J=8.31 Hz), 7.36 (2H, d, J=−8.33 Hz), 7.28 (5H, m), 7.16 (1H, d, J=8.12 Hz), 5.09 (1H, t, J=−3.14 Hz), 4.82 (1H, m), 4.58 (1H, m), 4.12 (2H, m), 3.32 (1H, t, J=12.6 Hz), 3.13 (1H, d, J=11.86 Hz), 2.65-0.93 (15H, m). MS-EI (m/z): 505.1825 [M+H]+.

Example 26 Synthesis of (R)-isopropyl-4-phenyl-2((R)-(4-methylphenyl)sulfonylthiazine-3-aminoformyl)butyrate (Compound 26)

The product (1.62 g, yield: 64%) as a white solid was obtained in accordance with the steps in Example 5, by using 1.55 g (7 mmol) D-homophenylalanine isopropyl ester as Raw material 2.

m.p. 88-90° C. $^1$H-NMR (400 MHz, CDCl$_3$) δ: 7.76 (2H, d, J=8.33 Hz), 7.36 (2H, d, J=−8.33 Hz), 7.26 (5H, m), 7.14 (1H, d, J=8.12 Hz), 5.06 (1H, t, J=3.14 Hz), 4.84 (1H, m), 4.53 (1H, m), 4.08 (2H, m), 3.31 (1H, t, J=12.6 Hz), 3.11 (1H, d, J=11.84 Hz), 2.65-0.93 (15H, m). MS-EI (m/z): 505.1825 [M+H]+.

Example 27 Synthesis of L-4-p-ethylbenzenesulfonyl-1,4-thiazin-3-carboxylic acid (Compound 27)

4.3 g oil was obtained in accordance with the steps in Example 4, by using 3.0 g p-ethylbenzenesulfonyl chloride in place of p-toluenesulfonyl chloride; yield: 92.5%, specific rotation $[\alpha]_D^{24.5}=-80.2°$ (H$_2$O).

$^1$H-NMR (400 MHz, CDCl$_3$) δ: 7.68354-7.66122 (d, 2H), 7.30423-7.26221 (m, 2H), 5.12202-5.10518 (m, 1H), 4.03122-3.99012 (m, 1H), 3.46436-3.40624 (m, 1H), 3.02103-2.99122 (m, 2H), 2.76654-2.73502 (m, 1H), 2.42466-2.37862 (m, 4H), 1.86453-1.82354 (t, 3H). MS (FAB) m/z: 315.4.

Example 28 Synthesis of (3R)-4-[(4-ethylbenzenesulfonyl)]-1,4-thiazin-3-carbonyl-L-leucine isopropyl ester (Compound 28)

In accordance with the steps in Example 5, D-leucine isopropyl ester hydrochlorate was reacted with 2.45 g L-4-p-ethylbenzenesulfonyl-1,4-thiazin-3-carboxylic acid, to obtain 2.08 g colorless oil.

$^1$H-NMR (400 MHz, CDCl$_3$) δ: 7.7681-7.7474 (d, 2H), 7.3793-7.3589 (m, 2H), 6.7543-6.7326 (d, 1H), 5.0288-4.9980 (m, 2H), 4.7738 (m, 1H), 4.6267-4.6042 (m, 1H), 4.2673-4.2301 (m, 1H), 3.5295-3.5176 (m, 1H), 3.1029 (m, 1H), 2.7532-2.7023 (m, 2H), 2.5487-2.5144 (m, 2H), 2.2188-2.1888 (m, 1H), 1.5826-1.4237 (m, 1H), 1.4047-1.3605 (m, 1H), 1.2821-1.2246 (m, 8H), 0.9178-0.9024 (m, 6H). MS (FAB) m/z: 470.4.

Example 29 Evaluation of the Neurotrophic Activity of Compounds

The neurotrophic activity of the compounds according to the invention can be embodied in multiple in vitro biological models, such as in vitro serum-free culture model of chick embryonic dorsal root ganglion.

Experimental method: in a sterile environment, chick embryo, which had been incubated for 8 d, had the spinal and bilateral ganglion exposed under anatomical lens. Dorsal root ganglions were picked one by one using sharp forceps, and seeded in culture bottles spread with rat tail collagen, at a density of 5-6 ganglions per bottle, and two bottles for each dose. After attachment culture in a 37° C., 5% $CO_2$ incubator for 1 h, serum-free medium DMEM containing nerve growth factor (NGF) (0.15 ng/mL), and the compound according to the invention were added. In the control group, only the medium and the same dose of NGF were added. After culture in the incubator for 48 h, the growth of neurite around dorsal root ganglion was observed under inverted phase contrast microscope, which was scored depending on the length and density of neurite.

Evaluation criteria: 0: no neurite; 1: rare long neurite; 2: relatively long or dense neurite; 3: long and dense neurite.

Table 1 shows the scores of the growth of neurites of chick embryo dorsal root ganglion promoted by the compounds in different doses, wherein the value is the average value of five ganglions.

TABLE 1

Evaluation results on chick embryo dorsal root ganglion-promoting activity of the compounds according to the invention

| Group | Average score |
|---|---|
| medium + NGF (0.15 ng/mL) (control group) | 0.33 |
| Compound 5 (1 pM) + NGF (0.15 ng/mL) | 0.65 |
| Compound 5 (100 pM) + NGF (0.15 ng/mL) | 1.55 |
| Compound 6 (1 pM) + NGF (0.15 ng/mL) | 1.68 |
| Compound 6 (100 pM) + NGF (0.15 ng/mL) | 2.55 |
| Compound 7 (1 pM) + NGF (0.15 ng/mL) | 1.46 |
| Compound 7 (100 pM) + NGF (0.15 ng/mL) | 1.95 |
| Compound 8 (1 pM) + NGF (0.15 ng/mL) | 1.78 |
| Compound 8 (100 pM) + NGF (0.15 ng/mL) | 2.45 |
| Compound 9 (1 pM) + NGF (0.15 ng/mL) | 1.76 |
| Compound 9 (100 pM) + NGF (0.15 ng/mL) | 2.56 |
| Compound 10 (1 pM) + NGF (0.15 ng/mL) | 1.54 |
| Compound 10 (100 pM) + NGF (0.15 ng/mL) | 2.38 |
| Compound 11 (1 pM) + NGF (0.15 ng/mL) | 1.86 |
| Compound 11 (100 pM) + NGF (0.15 ng/mL) | 2.65 |
| Compound 12 (1 pM) + NGF (0.15 ng/mL) | 1.77 |
| Compound 12 (100 pM) + NGF (0.15 ng/mL) | 2.48 |
| Compound 13 (1 pM) + NGF (0.15 ng/mL) | 1.96 |
| Compound 13 (100 pM) + NGF (0.15 ng/mL) | 2.88 |
| Compound 14 (1 pM) + NGF (0.15 ng/mL) | 1.44 |
| Compound 14 (100 pM) + NGF (0.15 ng/mL) | 2.35 |
| Compound 15 (1 pM) + NGF (0.15 ng/mL) | 1.78 |
| Compound 15 (100 pM) + NGF (0.15 ng/mL) | 2.68 |
| Compound 16 (1 pM) + NGF (0.15 ng/mL) | 1.57 |
| Compound 16 (100 pM) + NGF (0.15 ng/mL) | 2.69 |
| Compound 17 (1 pM) + NGF (0.15 ng/mL) | 1.75 |
| Compound 17 (100 pM) + NGF (0.15 ng/mL) | 2.71 |
| Compound 18 (1 pM) + NGF (0.15 ng/mL) | 1.66 |
| Compound 18 (100 pM) + NGF (0.15 ng/mL) | 2.68 |
| Compound 19 (1 pM) + NGF (0.15 ng/mL) | 1.55 |
| Compound 19 (100 pM) + NGF (0.15 ng/mL) | 2.49 |
| Compound 20 (1 pM) + NGF (0.15 ng/mL) | 2.10 |
| Compound 20 (100 pM) + NGF (0.15 ng/mL) | 3.32 |
| Compound 21 (1 pM) + NGF (0.15 ng/mL) | 1.79 |
| Compound 21 (100 pM) + NGF (0.15 ng/mL) | 2.74 |
| Compound 22 (1 pM) + NGF (0.15 ng/mL) | 1.88 |
| Compound 22 (100 pM) + NGF (0.15 ng/mL) | 2.78 |
| Compound 23 (1 pM) + NGF (0.15 ng/mL) | 2.12 |
| Compound 23 (100 pM) + NGF (0.15 ng/mL) | 3.21 |
| Compound 24 (1 pM) + NGF (0.15 ng/mL) | 1.89 |
| Compound 24 (100 pM) + NGF (0.15 ng/mL) | 2.80 |
| Compound 25 (1 pM) + NGF (0.15 ng/mL) | 1.76 |
| Compound 25 (100 pM) + NGF (0.15 ng/mL) | 2.68 |
| Compound 26 (1 pM) + NGF (0.15 ng/mL) | 1.80 |
| Compound 26 (100 pM) + NGF (0.15 ng/mL) | 2.78 |
| Compound 28 (1 pM) + NGF (0.15 ng/mL) | 2.00 |
| Compound 28 (100 pM) + NGF (0.15 ng/mL) | 2.96 |

It can be seen from the results above that the compounds according to the invention were superior to Compound 5 in terms of neurotrophic activity, and is superior to or comparable to Compound 6 in terms of activity, for example: at the doses of 1 pM and 100 pM, Compound 20 had the neurotrophic activity increased by 25% and 30% compared to Compound 6, respectively.

In view of the structure of compounds, R1 had a significant effect on the neurotrophic activity of compounds. For example, Compound 6 and Compound 28 were the same with respect to R2 and R3, respectively, while Compound 28 had ethyl as R1, and Compound 6 had methyl as R1. At the doses of 1 pM and 100 pM, Compound 28 had the neurotrophic activity increased by 19% and 16% compared to Compound 6, respectively. Therefore, it can be seen that with the increase in the carbon number of R1, the neurotrophic activity of thiazideamide derivatives increased.

In another aspect, R2 also had a significant effect on the neurotrophic activity of compounds. For example, Compounds 24, 25 and 26 were the same as Compound 6 with respect to R1 and R3, respectively, while Compound 24 had benzyl as R2, Compound 25 and 26 had phenethyl as R2, and Compound 6 had isobutyl as R2. At the doses of 1 pM and 100 pM, Compounds 24, 25 and 26 had the neurotrophic activity increased by 4.8-12.5% and 5.1-9.8% compared to Compound 6. This indicates that with the increase in the volume and/or hydrophobicity of R2, the neurotrophic activity of thiazideamide derivatives also increased.

Example 30 Evaluation of Compounds for In Vivo Pharmacodynamics on Apoplexy

1. Experimental Solution

In the Example, Kunmin mice were used as experimental subjects, intragastric (i.g.) administration was used, mouse BCAO-LBP (bilateral carotid artery occlusion with low blood pressure) model was used, and by determining neurological function score and the cerebral malondialdehyde (MDA) content in mice, the compounds were investigated for their protective effects on incomplete global cerebral ischemia in mice when administered prophylactically.

2. Experimental Method 2.1 Drug Preparation 2.1.1 Preparation of 0.7% carboxymethylcellulose sodium (CMC-Na) solution: one day before use, 0.7 g CMC-Na dry powder was weighed, and added to 100 ml distilled water. The mixture was heated appropriately under stirring until CMC-Na was completely dissolved. After standing overnight, the mixture was mixed well, and sealed and packaged.

2.1.2 Preparation of a drug for intragastric administration: the compound was prepared to a 1.5 mg/ml solution using 0.7% CMC-Na solution.

2.2 Grouping and Administration 28 mice, which had adapted to the laboratory environment for 1 week, were evenly grouped depending on body weight. The mice were intragastrically administered with 0.7% CMC-Na or one of the compounds, once/d, for 3 d. The groups were as followed:

Sham-operated group: 4 mice, intragastrically administered with 0.7% CMC-Na solution;

Brain ischemia model group: 12 mice, intragastrically administered with 0.7% CMC-Na solution;

Administration group: 12 mice, intragastrically administered at a dose of 0.2 ml/10 g, i.e., the dose of the compound was 30 mg/kg.

2.3 Incomplete Global Cerebral Ischemia of Mice and Determination of the Cerebral MDA Content 2.3.1 Mouse bilateral carotid artery ligation: 1 h after the last administration, the mice were subjected to orbital bloodletting to reduce blood pressure (which was about 30% of the total blood volume of the mice), and then fixed in supine position on the operating table, and cut in the middle of neck. Carotid artery was subjected to blunt dissection, and 2 lines were used in ligation for each side. The time counting started after the ligation with the third line, the carotid artery was cut off between the two lines, and the incision was sewn up. In the Sham-operated group, the carotid artery was only separated without ligation. After the operation, the mice were unfixed quickly, and the mice were observed and recorded for the behaviors within 6 h (scoring depending on the following table using blind method) and the death time. The brains were taken quickly after the mice died, the cerebellums were removed, and the MDA content in the whole cerebrum was determined by thiobarbituric acid (TBA). The mice, which did not die 6 h later, were killed, and the brains were taken.

2.3.2 Neurological function score: the scoring criteria are shown in Table 2

TABLE 2

Neurological behavior evaluation form

| | |
|---|---|
| (1) Placing mice on the ground (if the following behaviors occur simultaneously, the most severe one is recorded; if the mice did not move, the mice can be stimulated by gently pushing the buttocks) normal movement | 4 points 0 point |
| curved-path walking, but without rotation (showing no tail-chasing) | 1 point |
| rotation, showing tail-chasing (recording the rotation direction, clockwise or anticlockwise) | |
| rotating for 1-2 times | 1 point |
| rotating for 3-5 times | 2 points |
| rotating for more than 5 times | 3 points |
| rolling (recording the rolling direction, left or right) rolling for 1-2 times | 1 point |
| rolling for 3-5 times | 2 points |
| rolling for more than 5 times | 3 points |
| hemiplegia (receding the direction of hemiplegia, left or right) | 4 points |
| (2) Abnormal movement | 8 points |
| dysmyotonia (involuntary twist, causing sustained, generally very weird posture), seizure disorder (sudden loss of consciousness, falling down, head hypsokinesis, rigidity of limbs), myoclonus (convulsion) | 1 point |
| excitation (jumping) jumping for 1-2 times | 1 point |
| jumping for 3-5 times | 2 points |
| jumping for more than 5 times | 3 points |
| holding still and/or gasping (if there is hemiplegia, it is recorded as hemiplegia) | 2 points |
| 4 points: died immediately after operation (within 10 min) | |
| (3) Absence of reflex | 1 point |
| auricle reflex (a mouse will shake its head when its ear canal is touched) | 1 point |
| Total: | 13 points |

2.3.3 Determination of the cerebral MDA content in mice:
The cerebra of mice were taken and weighed, and were prepared into 15% brain homogenate using N.S. 1.2 ml brain homogenate was placed in a 37° C. water bath for 1 h (shaking once every 10 min) and then taken out. 20% trichloroacetic acid 0.6 ml was added, and the mixture was mixed well, and was on standing for 10 min. After centrifugation at 2000 rpm for 10 min, to 1.2 ml supernatant, 0.67% TBA 0.6 ml was added. The mixture was placed in a boiling water bath for 10 min, and was taken out for cooling, and the OD value at a wavelength of 532 nm was determined.

3. Statistical Analysis
The experimental data was expressed as $\bar{x} \pm SEM$; SPSS 13.0 statistic software was used. Homogeneity or heterogeneity of variance was determined by one-factor analysis of variance. In the case of homogeneity of variance, LSD test was used; in the case of heterogeneity of variance, Dunnett's T3 test was used. Significant difference among different groups was compared, and P<0.05 indicated statistical significance. The results were shown in Table 3.

TABLE 3

Evaluation results on the MDA content and neurologic behavior score of compounds in BCAO-LBP mice ($\bar{x} \pm SEM$)

| Group (i.g.) | Number of mice | MDA content (nmol/g) | Neurologic deficit score |
|---|---|---|---|
| Sham-operated group | 4 | 33.15 ± 2.75 | 0.00 ± 0.00 |
| Brain ischemia model group | 11 | 40.94 ± 1.754* | 3.92 ± 0.25** |
| Compound 5 | 12 | 36.09 ± 1.85 | 3.62 ± 0.31 |
| Compound 6 | 12 | 32.87 ± 0.95### | 2.08 ± 0.40## |
| Compound 8 | 11 | 34.95 ± 1.55## | 1.77 ± 0.28## |
| Compound 9 | 12 | 33.29 ± 1.81## | 2.37 ± 0.31# |
| Compound 11 | 12 | 32.57 ± 0.75### | 3.66 ± 0.31 |
| Compound 13 | 12 | 33.90 ± 1.45## | 2.47 ± 0.40# |
| Compound 15 | 12 | 33.77 ± 1.61## | 1.91 ± 0.28## |
| Compound 18 | 11 | 32.66 ± 0.93### | 2.65 ± 0.31# |
| Compound 20 | 11 | 34.90 ± 1.65## | 3.76 ± 0.31 |
| Compound 22 | 12 | 33.27 ± 1.61## | 3.08 ± 0.40 |
| Compound 23 | 12 | 31.87 ± 0.95### | 1.81 ± 0.26## |
| Compound 28 | 11 | 30.90 ± 1.65### | 1.87 ± 0.31## |

*p < 0.05, compared to Sham-operated group,
**p < 0.01, compared to Sham-operated group;
p < 0.05, compared to brain ischemia model group,
p < 0.01, compared to brain ischemia model group,
p < 0.001, compared to brain ischemia model group The results showed: the compounds according to the invention were superior to Compound 5 and/or Compound 6 in terms of protective effect on incomplete global cerebral ischemia in mice. The mice in the groups administered with Compounds 8, 15, 23, and 28 had the neurologic deficit score decreased by about 15%, 8%, 13%, and 10% compared to the mice in the group administered with Compound 6, respectively; the mice in the groups administered with Compound 9, 13, 18, and 22 had the neurologic deficit score decreased by about 35%, 32%, 27%, and 15% compared to the mice in the group administered with Compound 5. Therefore, compared to the existing compounds, the compounds according to the invention had the in vivo efficacy enhanced significantly in mice with apoplexy.

It could be found by analysis of the structures of compounds that a change in R1 and/or R2 would influence the above efficacy of the compounds. It could be found by comparison between Compound 28 and Compound 6, and comparison between Compound 23 and Compound 6 that: an increase in the number of carbon atoms of R1, or an increase in the volume and/or hydrophobicity of R2, promoted the in vivo efficacy on apoplexy.

Example 31 Evaluation of Compounds for Passing Through Blood-Brain Barrier

1. Experimental Solution
MDCK-MDR1 cells were monolayer cells which highly express P-gp transporter after transfection of MDCK (Madin-Darby canine kidney epithelial cell) with MDR1 gene. Due to its density and high expression of efflux protein, the monolayer has similarity compared to blood-brain barrier (BBB) structure and now can be used as one of models for evaluating the ability of passing through BBB. In the invention, MDCK-MDR1 cells were used to study the membrane permeability of the compounds according to the invention, and to primarily evaluate its ability of passing through BBB.

2. Experimental Method
2.1 Preparation of Solutions
Preparation of medium: to Dulbecco's modified eagle medium (DMEM), 10% fetal bovine serum (FBS), 1% glutamine, 100 U·mL$^{-1}$ penicillin-streptomycin double antibody solution, 1% nonessential amino acid, and geneticin (G418) 1.2 mg·L$^{-1}$ were added immediately prior to use.

Preparation of a digestion solution: to the weighed trypsin 1 g and ethylenediaminetetraacetic acid (EDTA) 80 mg, 400 mL phosphate buffer (PBS) was added, filtration sterilization was carried out using a 0.22 μm filter membrane, and the resultant solution was stored at −20° C. for further use.

Preparation of a glutamine stock solution: to glutamine 2.92 g, 100 mL PBS was added, filtration sterilization was carried out using a 0.22 μm filter membrane, and the resultant solution was sub-packed by 1 mL, and stored at −20° C. for further use.

Preparation of a penicillin-streptomycin stock solution: to penicillin 0.8 million U, 20 mL physiological saline was added, and to streptomycin 1 million U, 25 mL physiological saline was added. The two solutions were mixed well at a ratio of 1:1, filtration sterilization was carried out using a 0.22 μm filter membrane, and the resultant solution was sub-packed by 1 mL, and stored at −20° C. for further use.

Preparation of Hank's Balanced Salt Solution (HBSS): NaCl 8.0 g, KCl 0.4 g, Na$_2$HPO$_4$.H$_2$O 0.0475 g, KH$_2$PO$_4$ 0.06 g, and 4-(2-hydroxyethyl)piperazine-1-ethanesulfonic acid (HEPES) 6 g, were dissolved in ultrapure water, pH value was adjusted to 7.2-7.4, water was added to a total volume of 1 L, filtration sterilization was carried out using a 0.22 μm filter membrane, and the resultant solution was stored at −20° C. for further use.

2.2 Cell Culture

The frozen MDCK-MDR1 cells were quickly thawed in a 37° C. water bath. To the resuscitated cells, DMEM medium containing 10% FBS was added, and the cells were cultured in an incubator at 37° C., 5% CO$_2$, and a relative humidity of 90%. The medium was changed every other day. After fusion of the cells growing for 1-2 days, the cells were digested with 0.25% trypsin-EDTA (0.2%) mixed digestion solution at 37° C., and were sub-cultured at a certain ratio. The cells for use in experiment were those passaged for 40-60 generations.

When the cell fusion degree reached 80%, the cells were digested and then suspended in complete medium, and seeded to Millicell plate at 1×10$^6$ cells·mL$^{-1}$. The medium was changed every other day, and 1 week later, the medium was changed every day. After culturing for 5 days, the resistance value reached a constant value (>200 Ω·cm$^2$), and the cells could be used in the transport experiment.

2.3 Quality Control of MDCK-MDR1 Cell Monolayer:

2.3.1 Determination of Transepithelial Electrical Resistance (TEER)

The electrode was dipped into DMEM medium and equilibrated for 24 h, and then taken out and sterilized by dipping into 70% alcohol for 15 min. The electrode was placed at room temperature and dried in air, and then equilibrated in sterile DMEM medium for 15 min. In the experiment, the two ends of the electrode were inserted into the upper and bottom wells of 24-well Millicell culture plate sequentially to determine resistance value, for three times at random site for each well, and the resistance values were recorded. Meanwhile, the resistance value of a blank well was also determined. The transepithelial electrical resistance (TEER) was calculated in accordance with the following equation.

TEER=$(R_t-R_0)\times S$ wherein, $R_t$ refers to a measured resistance value; $R_0$ refers to the resistance value of a blank well; S refers to an effective film area.

2.3.2 Positive Control Compound:

Rhodamine 123 (Rho-123), as positive control compound, was diluted to 5 μmol·L$^{-1}$ using HBSS, and the medium was removed from each well before the experiment. After washing with 37° C. HBSS twice, the cells were incubated in a 37° C. culture incubator, wherein Rho-123 was added to the upper wells, and HBSS was added to the bottom wells. The incubation was carried out in a constant temperature shaker, and the solutions from the bottom wells were collected at each time point (0 min, 30 min, 90 min, 120 min), and stored at −20° C. for further use. The amount of Rho-123 permeated to the bottom well was determined by fluorospectrophotometer, wherein the emission wavelength was 430 nm, and the excitation wavelength was 530 nm. In the experiment, the $P_{app}$ value of Rho-123 was consistent with the value reported in papers.

2.4 Drug Transport Experiment

Before the experiment, Millicell seeded with cells was immersed in 37° C. HBSS for a suitable period of time, and Millicell was washed gently to remove the substances attached on the cell surface.

The permeability from cavity-surface to basal surface: drug-containing HBSS 0.35 mL was add to Apical (AP), and blank HBSS 1.2 mL was added to Basolateral (BL). The Millicell was placed at 37° C. in a shaker under shaking at 50 r·min$^{-1}$, 50 μL sample was collected from the bottom well at 0, 30, 90, 120 min, respectively, and the same volume of blank HBSS was supplemented. 3 wells were set for each concentration, and to the sample, an internal standard solution (50 μL) and ethyl acetate (350 μL) were added precisely. The mixture was mixed homogeneously under shaking, and centrifuged at 12000 rmp for 5 min. The supernatant (300 μL) was volatilized to dryness, and re-dissolved in 50 μL acetonitrile. The 10 μL resultant solution was used for determination.

The permeability from basal surface to cavity surface: the drug is added to Basolateral (BL), and blank HBSS was added to Apical (AP), and the other steps were the same as those of the experiment for determining the permeability from cavity-surface to basal surface.

The apparent permeability coefficient ($P_{app}$) of a drug reflects the ability of the drug to pass through cell monolayer and the drug absorption rate and extent. It can be calculated in accordance with the following equation:

$$P_{app} = \frac{\Delta Q}{\Delta t \cdot A \cdot C_0}$$

wherein, Q represents the amount of drug permeated in the t period, A represents cell surface area, and represents the area (0.6 cm$^2$) of supporting film in this model, and $C_0$ represents an initial concentration. The unit of $P_{app}$ is expressed as cm·s$^{-1}$.

2.5 Sample Measurement

By measurement using LC/MS, the concentration of each sample was quantitated using its standard curve (50 nM-10000 nM).

3. Experimental Results

The measurement results on the apparent permeability coefficient of compounds are shown in Table 4.

TABLE 4

The apparent permeability coefficient of compounds

| Drug | $P_{app}$ (×10$^{-6}$) |
|---|---|
| Rhodamine 123 | 4.89 |
| Compound 5 | 8.38 |
| Compound 6 | 39.5 |
| Compound 7 | 49.8 |
| Compound 8 | 19.2 |
| Compound 9 | 12.4 |
| Compound 10 | 34.1 |
| Compound 11 | 15.6 |
| Compound 12 | 22.5 |
| Compound 13 | 18.9 |
| Compound 14 | 33.2 |
| Compound 15 | 40.8 |
| Compound 16 | 39.7 |
| Compound 17 | 22.7 |
| Compound 18 | 28.5 |
| Compound 19 | 42.3 |
| Compound 20 | 18.8 |
| Compound 21 | 25.8 |
| Compound 22 | 40.6 |
| Compound 23 | 44.2 |
| Compound 24 | 37.8 |
| Compound 25 | 27.3 |
| Compound 26 | 35.9 |
| Compound 28 | 45.8 |

As seen from Table 4, the compounds according to the invention were superior to Compound 5 in terms of the ability of passing through blood-brain barrier, and was superior to or comparable to Compound 6. Compounds 7, 23 and 28 had $P_{app}$ value increased by above 7% compared to Compound 6. The results show that the compounds according to the invention had good ability of passing through blood-brain barrier.

Although the embodiments of the invention have been described in detail, a person skilled in the art would understand that according to all the disclosed teachings, details can be amended and modified, and these alterations all fall into the protection scope of the invention. The scope of the invention is defined by the claims and any equivalent thereof.

The invention claimed is:

1. A compound, or a pharmaceutically acceptable salt or solvate thereof, wherein the compound is selected from:

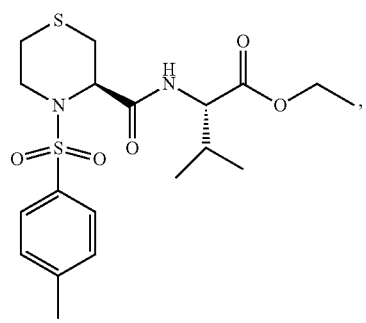

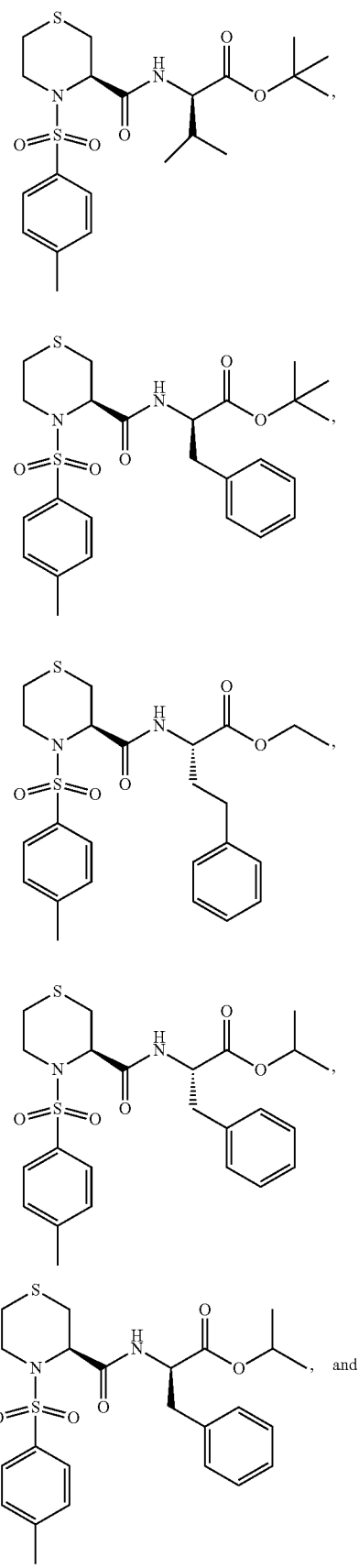

-continued

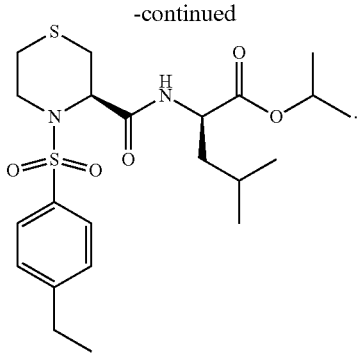

2. A pharmaceutical composition comprising the compound, or a pharmaceutically acceptable salt or solvate thereof according to claim 1;
optionally, the pharmaceutical composition further comprises one or more pharmaceutically acceptable carriers and/or excipients.

3. A method for treating, in a subject in need thereof, one or more diseases or traumas selected from the group consisting of:

(1) a neurodegenerative disease selected from the group consisting of Alzheimer's disease, Parkinson's disease, Huntington's disease, amyotrophic lateral sclerosis and marrowbrain multiple sclerosis;

(2) a physical trauma selected from the group consisting of heat injury, cold injury, mechanical injury and electric injury; and (3) a disease selected from the group consisting of acquired immunodeficiency, diabetes mellitus and stroke, the method comprising administering a therapeutically effective amount of the compound, or a pharmaceutically acceptable salt or solvate thereof according to claim 1, or a pharmaceutical composition comprising the compound, or a pharmaceutically acceptable salt or solvate thereof, to the subject in need thereof.

4. The method according to claim 3, wherein the subject is a mammal.

5. The method according to claim 3, wherein the subject is human.

* * * * *